(12) United States Patent
Kumar T. K. et al.

(10) Patent No.: US 8,212,063 B2
(45) Date of Patent: Jul. 3, 2012

(54) XANTHOPHYLL COMPOSITION CONTAINING TRANS, MESO-ZEAXANTHIN, TRANS, R, R-ZEAXANTHIN AND TRANS, R, R-LUTEIN USEFUL FOR NUTRITION AND HEALTH CARE AND A PROCESS FOR ITS PREPARATION

(75) Inventors: Sunil Kumar T. K., Angamally South (IN); Sherena P. Abdulkadir, Angamally South (IN); Shankaranarayana Madapura Lingappiah, Angamally South (IN)

(73) Assignee: OmniActive Health Technologies Limited, Thane (IN)

( * ) Notice: Subject to any disclaimer, the term of this patent is extended or adjusted under 35 U.S.C. 154(b) by 706 days.

(21) Appl. No.: 11/800,317

(22) Filed: May 4, 2007

(65) Prior Publication Data
US 2007/0265351 A1 Nov. 15, 2007

(30) Foreign Application Priority Data
May 10, 2006 (IN) .......................... 727/MUM/2006

(51) Int. Cl.
*C07C 69/02* (2006.01)
(52) U.S. Cl. ............ 554/230; 554/21; 554/20; 514/548; 514/552; 514/725; 514/729; 424/439
(58) Field of Classification Search .................. 514/729, 514/548, 552, 725; 554/21, 20, 230; 424/439
See application file for complete search history.

(56) References Cited

U.S. PATENT DOCUMENTS

| | | | |
|---|---|---|---|
| 5,382,714 A | 1/1995 | Khachik et al. | |
| 5,523,494 A | 6/1996 | Torres-Cardona et al. | |
| 5,780,693 A * | 7/1998 | Bernhard et al. ............ | 568/816 |
| 5,973,211 A | 10/1999 | Rodriguez | |
| 6,218,436 B1 | 4/2001 | Howard et al. | |
| 6,329,432 B2 | 12/2001 | Howard et al. | |
| 6,376,722 B1 | 4/2002 | Sanz et al. | |
| 6,743,954 B2 | 6/2004 | Ernst et al. | |
| 2004/0044085 A1 | 3/2004 | Kumar T.K. et al. | |
| 2005/0031736 A1 * | 2/2005 | Nguyen et al. .................. | 426/72 |

FOREIGN PATENT DOCUMENTS

| | | |
|---|---|---|
| EP | 1 911 742 | 4/2008 |
| WO | 01/83414 | 11/2001 |
| WO | 2007/076416 | 7/2007 |
| WO | 2007/098520 | 9/2007 |

OTHER PUBLICATIONS

Landrum, et al., "Lutein, Zeaxanthin, and the Macular Pigment", Archives of Biochemistry and Biophysics, vol. 385, No. 1, Jan. 1, 2001, pp. 28-40.
Handelman, et al., "Measurement of Carotenoids in Human and Monkey Retinas", Methods in Enzymology, vol. 213, 1992, pp. 220-231.
Bone, et al., "Distribution of Macular Pigment Components, Zeaxanthin and Lutein, in Human Retina", Methods in Enzymology, vol. 213, 1992, pp. 360-367.
Khachik, et al., "Identification of Lutein and Zeaxanthin Oxidation Products in Human and Monkey Retinas", Investigative Ophthalmology & Visual Science, Aug. 1997, vol. 38, No. 9, pp. 1802-1810.
Billsten, et al., "Photophysical Properties of Xanthophylls in Carotenoproteins from Human Retina", Photochemistry and Photobiology, 2003, 78(2):138-145.
Landrum, et al., "Dietary Lutein Supplemenation Increases Macular Pigment (MP)", The FASEB Journal, vol. 10, No. 3, Mar. 8, 1996, p. A242.
Breithaupt, et al., "Comparison of plasma responses in human subjects after the ingestion of 3$,3R'-zeaxanthin dipalmitate from wolfberry (*Lycium barbarum*) and non-esterified 3R, 3R'-zeaxanthin using chiral high-performance liquid chromatography", British Journal of Nutrition (2004), 91, 707-713.
Bone, et al., "Lutein and Zeaxanthin Dietary Supplements Raise Macular Pigment Density and Serum Concentrations of these Carotenoids in Humans", J. Nutr. 133:992-998, Apr. 2003.
Khachik, et al., "Isolation and structural elucidation of the geometrical isomers of lutein and zeaxanthin in extracts from human plasma", Journal of Chromatography, 582 (1992) 153-166.
Khachik, et al., "Dietary Carotenoids and their Metabolites as Potentially Useful Chemoprotective Agents against Cancer", Antioxidant Food Supplements in Human Health, Academic Press, 1999, pp. 203-215.
Landrum, et al., "Meso-zeaxanthin: a cutting-edge carotenoid", Functional Foods and Nutraceuticals, Sep. 10, 2001.
Khachik, Frederick, "An Efficient Conversion of (3R,3'R,6'R)-Lutein to (3R,3'S,6'R)-Lutein (3'-Epilutein) and (3R,3'R)-Zeaxanthin", J. Nat. Prod. 2003, 66, 67-72.
Maoka, et al., "The First Isolation of Enantromeric and *Meso-*Zeaxanthin in Nature", Comp. Biochem. Physiol. vol. 83B, No. 1, pp. 121-124, 1986.
von P. Karrer, et al., "Umwandlung von α-Carotin in β-Carotin and von Xanthophyll' in Zeaxanthin", Helvetica Chimica Acta., 1947, p. 266.
Andrewes, A.G., "Isomerization of ε-Carotene to β-Carotene and of Lutein to Zeaxanthin", Acta Chem. Scand. B 28, 1974, No. 1, 137-140.
Adams, et al., "The FEMA GRAS assessment of benzyl derivatives used as flavor ingredients", Food and Chemical Toxicology 43 (2005) 1207-1240.

(Continued)

*Primary Examiner* — Sudhakar Katakam
(74) *Attorney, Agent, or Firm* — Hamre, Schumann, Mueller & Larson, P.C.

(57) ABSTRACT

The present invention relates to a xanthophyll composition containing (trans, meso)-zeaxanthin), (trans, R,R)-zeaxanthin and (trans, R,R)-lutein useful for nutrition and health care and a process for its preparation. More particularly, the invention relates to a xanthophylls composition containing at least 80% by weight of total xanthophylls, out of which the (trans,3R,3'S, meso)-zeaxanthin content is at least 80%, the remaining being (trans, R,R)-zeaxanthin, (trans, R,R)-lutein and trace amounts of other carotenoids. This invention further provides a xanthophyll composition containing at least 80% by weight of total xanthophylls, out of which at least 50% being (trans, R,R)-zeaxanthin, the remaining being (trans,3R, 3'S, meso)-zeaxanthin, (trans, R,R)-lutein and trace amounts of other carotenoids.

22 Claims, 3 Drawing Sheets

OTHER PUBLICATIONS

Ernest, et al., "Recent advances in industrial carotenoid synthesis", Pur Apl. Chem, vol. 74, No. 8, pp. 1369-1382, 2002.

Lutnaes, et al., "Is (9Z)-"meso"-Zeaxanthin Optically Active?", Chirality 13:224-229 (2001).

Bone, et al., "Macular pigment response to a supplement containing meso-zeaxanthin, lutein and zeaxanthin", Nutrition & Metabolism, BioMed Central, vol. 4, No. 1, May 2007.

Karrer, et al., "Cis-trans isomerism of carotenoids", Carotenoids, Elsevier Publishing Company, Inc., New York, 1950, Chapter 5, pp. 38-42.

International Search Report issued in PCT/IN2007/000327 mailed Jul. 2, 2008.

* cited by examiner

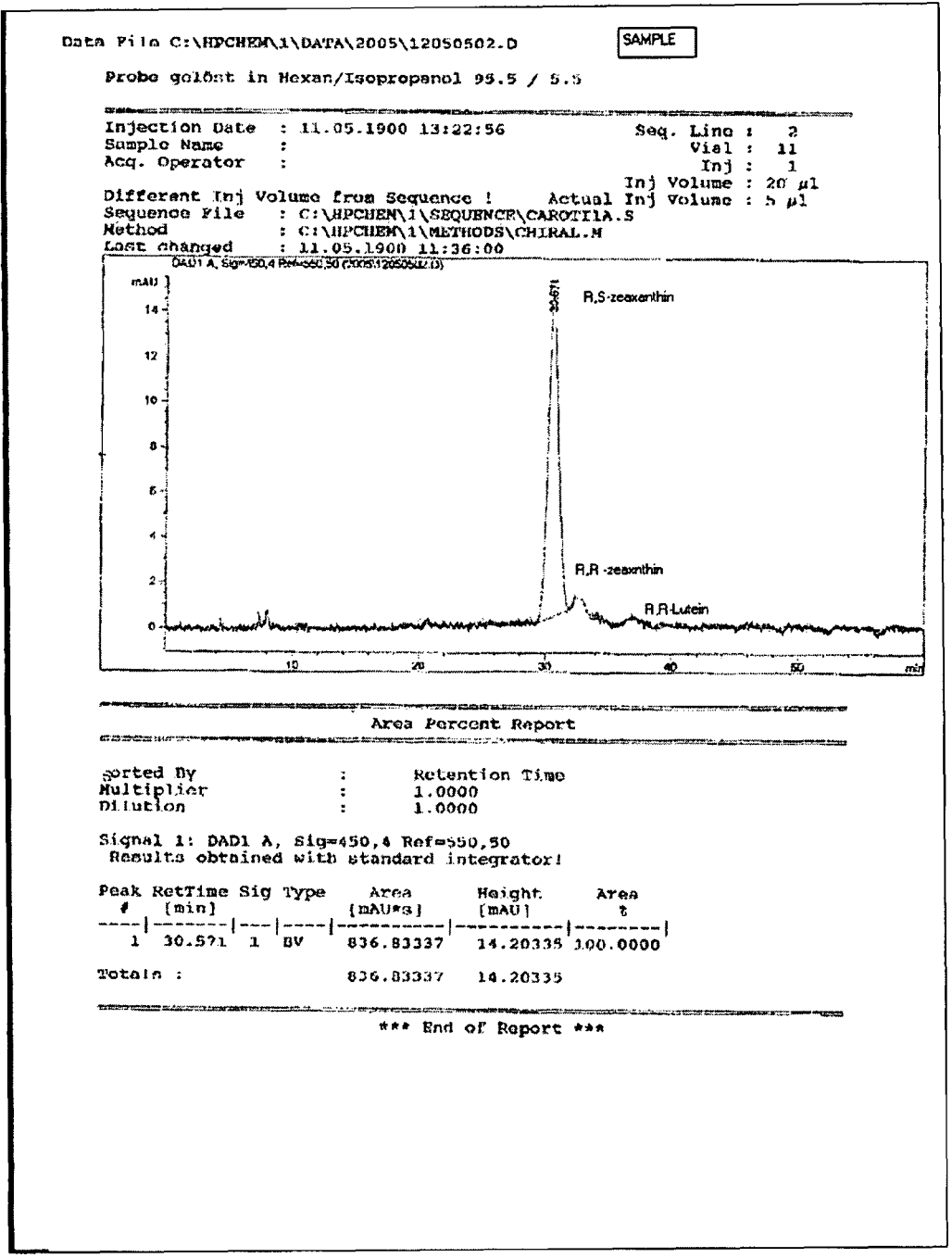
Fig-1 Chiral HPLC chromatogram of xanthophylls composition containing (trans,R,S)-meso-zeaxanthin sample.

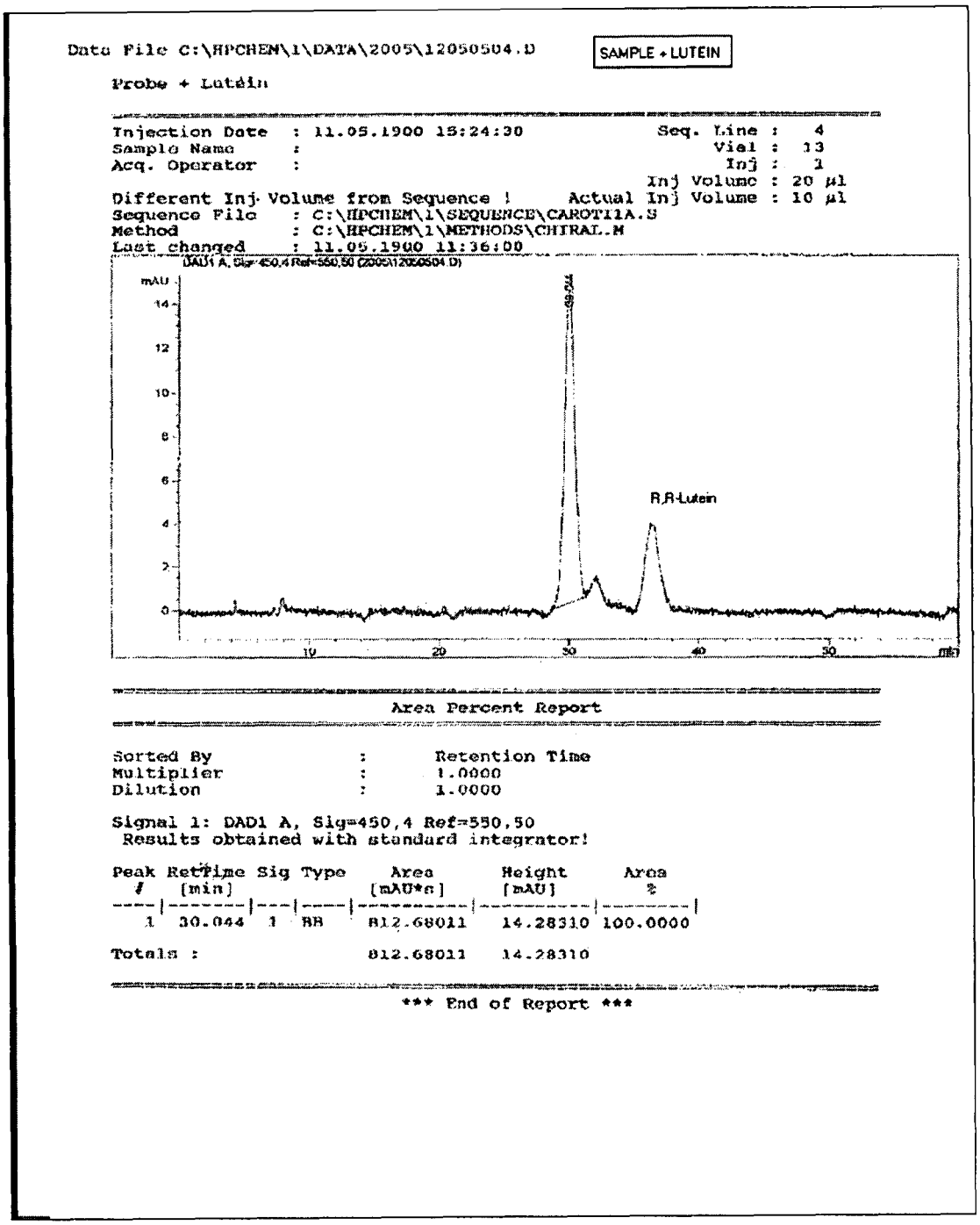
Fig-2 Chiral HPLC chromatogram of xanthophylls composition containing (trans,R,S)-meso-zeaxanthin sample along with added (trans-3R,3'R,6'R )-lutein

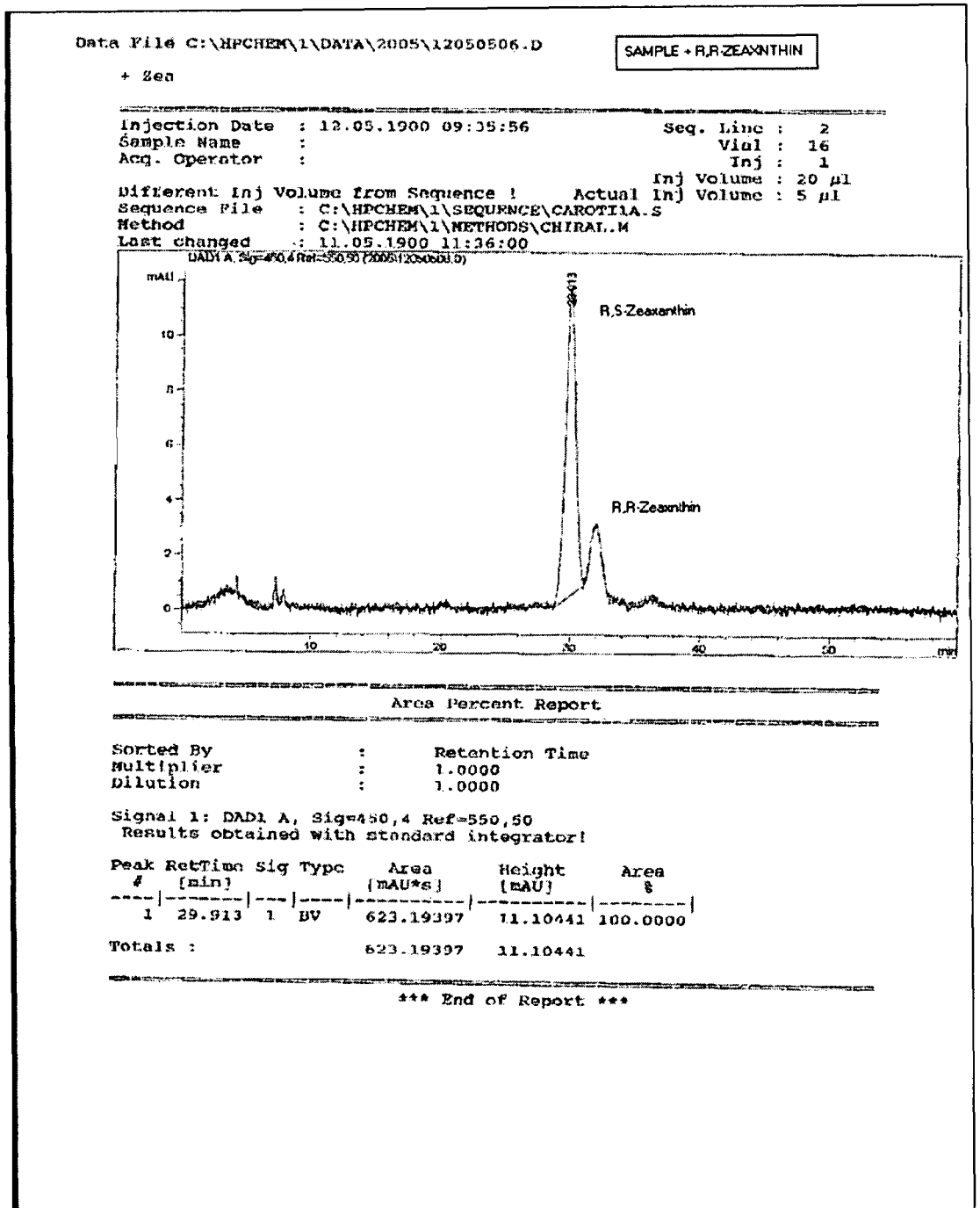
Fig-3 Chiral HPLC chromatogram of xanthophylls composition containing (trans,R,S)-meso-zeaxanthin sample + (trans-3R,3'R)--zeaxanthin.

XANTHOPHYLL COMPOSITION CONTAINING TRANS, MESO-ZEAXANTHIN, TRANS, R, R-ZEAXANTHIN AND TRANS, R, R-LUTEIN USEFUL FOR NUTRITION AND HEALTH CARE AND A PROCESS FOR ITS PREPARATION

FIELD OF THE INVENTION

The present invention relates to a xanthophyll composition containing (trans, meso)-zeaxanthin), (trans, R,R)-zeaxanthin and (trans, R,R)-lutein useful for nutrition and health care and a process for its preparation. More particularly, the invention relates to a xanthophylls composition containing at least 80% by weight of total xanthophylls, out of which the (trans,3R,3'S, meso)-zeaxanthin content is at least 80%, the remaining being (trans, R,R)-zeaxanthin, (trans, R,R)-lutein and trace amounts of other carotenoids. This invention further provides a xanthophyll composition containing at least 80% by weight of total xanthophylls, out of which at least 50% being (trans, R,R)-zeaxanthin, the remaining being (trans,3R, 3'S, meso)-zeaxanthin, (trans, R,R)-lutein and trace amounts of other carotenoids.

This invention further provides a xanthophyll composition containing at least 80% by weight of total xanthophylls, out of which at least 50% being (trans, R,R)-lutein, the remaining being (trans,3R,3'S, meso)-zeaxanthin, (trans, R,R)-zeaxanthin and trace amounts of other carotenoids.

The xanthophyll composition containing (trans,3R,3'S, meso)-zeaxanthin, (trans, R,R)-zeaxanthin and (trans, R,R)-lutein of the present invention is particularly useful for nutrition and health care.

BACKGROUND OF THE INVENTION

Carotenoids are yellow, red and orange pigments and are widely distributed in nature. Although specific carotenoids have been identified in various fruits and vegetables, bird feathers, egg-yolk, poultry skin, crustaceans and macular eye region, they are especially abundant in marigold petals, corn and leafy vegetables. The correlation between dietary carotenoids and carotenoids found in human serum and plasma indicate that only selected groups of carotenoids make their entry into the human blood stream to exert their effect. Each carotenoid shows an individual pattern of absorption, plasma transport and metabolism.

Carotenoids absorb light in the 400-500 nm region of the visible spectrum. This physical property imparts the characteristic yellow/red color to the pigments. Carotenoids contain a conjugated backbone composed of isoprene units, which are usually inverted at the center of the molecule, imparting symmetry. Changes in geometrical configuration about the double bonds result in the existence of many cis- and trans-isomers. Mammalian species do not synthesize carotenoids and therefore these have to be obtained from dietary sources such as fruits, vegetables and egg yolks. In the recent years, carotenoids have been reported to have several health benefits, which include prevention and/or protection against serious health disorders.

Carotenoids are non-polar compounds classified into two sub-classes, namely, polar compounds called xanthophylls or oxy-carotenoids and non-polar hydrocarbon carotenes like β-carotene, lycopene, etc. Both the sub-classes have at least nine conjugated double bonds responsible for the characteristic colors of the carotenoids. Xanthophylls have ring structures at the end of the conjugated double bond chain with polar functions like hydroxyl or keto group. The examples for xanthophylls include lutein, zeaxanthin, capsanthin, canthaxanthin, β-cryptoxanthin, astaxanthin, etc. As natural colorants and also for their role in human health, xanthophylls like lutein and zeaxanthin have attracted the renewed attention of scientists and researchers in the biomedical, chemical and nutritional field in recent years.

Lutein and zeaxanthin contribute to yellow and orange—yellow colours respectively. Lutein and zeaxanthin can be present in plant material in the free form and also in ester form. Lutein is present in green leafy vegetables like spinach, kale and broccoli in the free form; fruits like mango, orange and papaya; red paprika, algae, yellow corn, contain lutein in the form of its esters. It is also present in the blood stream and various tissues in human body and particularly in the macula, lens and retina of the eye.

Lutein is chemically designated as β,ε-carotene 3,3'-diol. Zeaxanthin is formed by the addition of two hydroxy groups to β-carotene. Since the hydroxy positions are in 3 and 3'-, the chemical name for zeaxanthin is β,β-carotene-3,3'-diol. The common name of zeaxanthin is derived from *zea mays* because this carotenoid was first identified in corn (*zea mays*).

It can be seen that lutein is not symmetrical as the position of double bond in the left ring is not identical with the double bond position in the right ring. Zeaxanthin is completely symmetrical with regards to left and right rings due to an extra conjugated double bond compared to lutein.

Xanthophylls can show both optical (R- and S-stereo isomers) and geometrical isomers (trans,E- and cis,Z-). The conformation of R- and S-stereo isomers is based on CD spectral and chiral column HPLC studies while the conformation of cis- and trans-isomers is based on electronic, infrared, NMR, HPLC-MS and HPLC-NMR on-line spectroscopy studies. It is well known that when an organic molecule has a carbon atom with four different types of atoms or groups attached to it, that carbon atom is designated as chiral carbon atom. The chiral carbon atom is responsible for two different spatial arrangements leading to formation of optical isomers while the number of double bonds of the polyene chain and the presence of a methyl group and the absence of steric hindrance decide the number of trans- and cis-isomers. In the case of trans-zeaxanthin, the carbon atoms at 3 and 3' positions in the two end rings are both chiral atoms. Thus, trans-zeaxanthin has two chiral centers at the carbon atoms C3 and C3', based on the positions of the secondary hydroxy groups attached to them. Therefore, there are four possible stereo isomers of trans-zeaxanthin namely, (3R-3'R)-isomer, (3S-3'S)-isomer and (3R-3'S)- or (3S-3'R)-isomer. In these isomers (3R-3'S)- & (3S-3'R) are identical. Thus, there are three chiral isomers of trans-zeaxanthin. The isomer causing rotation of polarized light in a right handed manner is called R-stereo isomer, the isomer causing left handed rotation S-stereo isomer and the third isomer possessing a two fold opposite effects (optically inactive) which is called meso-form of trans-zeaxanthin. These are shown in the formulae given below including the chemical structure of lutein

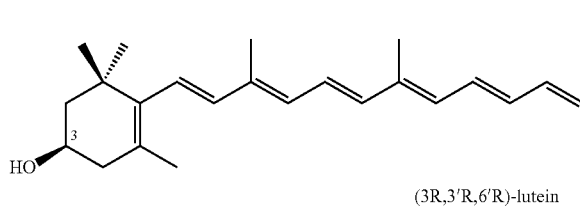

(3R,3'R,6'R)-lutein

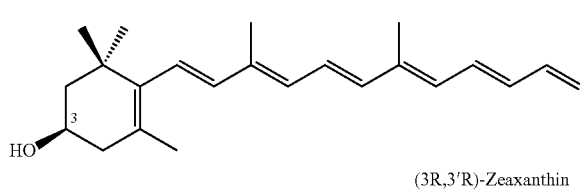

(3R,3'R)-Zeaxanthin

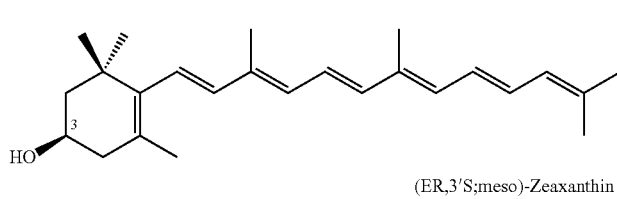

(ER,3'S;meso)-Zeaxanthin

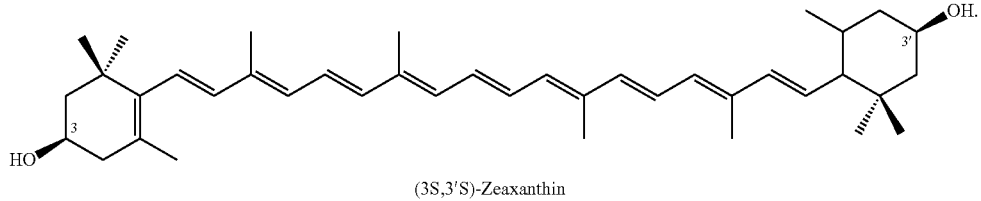

(3S,3'S)-Zeaxanthin

The conjugated double bonds of lutein and zeaxanthin contribute to the distinctive colours of each pigment, and also influence the ability of these to quench singlet oxygen. Due to the extra conjugated double bond, zeaxanthin is believed to be a stronger anti-oxidant compared to lutein.

The macular pigment of the eye is composed primarily of three xanthophylls pigments, namely (R,R)-lutein, (R,R)-zeaxanthin and (R,S)-zeaxanthin in the order 36, 18 and 18% of the total carotenoid content of the retina along with the remaining 20% consisting of minor carotenoids like oxo-lutein, epi-lutein and ε,ε-carotene 3,3'-dione (J. T. Landrum and R. A. Bone, Arch. Biochem Biophys, 385, 28(2001)). Although these xanthophyll pigments are found throughout the tissues of the eye, the highest concentration is seen in the macula lutea region of the retina, including a central depression in the retina called the fovea. The concentration of xanthophylls pigments increases progressively towards the center of the macula and in the fovea, the concentration of these xanthophyll pigments are approximately a thousand fold higher than in other human tissues. (Landrum et al., Analysis of zeaxanthin distribution within individual human retinas, Methods in Enzymology, L. Packer (editor) 213A, 457-467, Academic Press 1992). The fovea is a relatively small area within the macula, in which the cone photoreceptors reach their maximal concentration. About 50% of the total amounts of the xanthophylls is concentrated in the macula where zeaxanthin dominates over lutein by a ratio of 2:1 (Handelman et al., Measurements of carotenoids in human and monkey retinas, in Methods in Enzymology, L. Packer (editor) 213A, 220-230, Academic press, NY, 1992; Billsten et al., Photochemistry and photobiology, 78, 138-145, 2003). At the center of the retinal fovea, zeaxanthin is a 50:50 mixture of (trans-3R,3'R)-zeaxanthin and (trans-3R,3'S)-zeaxanthin along with small quantity of (3S,3'S)-zeaxanthin (J. T. Landrum and R. A. Bone, Arch. Biochem. Biophy., 385, 28 2001).

The fovea is particularly important for proper visual function (e.g., acuity) and disease and damage to this area is known to result in legal blindness. For example, age-related macular degeneration (AMD) is characterized by pathological changes in the retina, retinal pigment epithelium (RPE) and/or the choroid and preferentially affects the macular region of the retina. This is the leading cause of irreversible vision loss in the United States among those ≧65 y old and there is no established treatment available for most patients. The loss of central vision results in the possible inability to recognize faces, to read or drive a car and therefore has a significant effect on an individual's ability to live independently. There is ample epidemiologic evidence which supports a role for dietary intake of lutein and zeaxanthin in different isomeric forms in protection against age-related cataract and macular degeneration. The detection of oxidation products of lutein and zeaxanthin in the human retina supports the hypothesis that dietary lutein and zeaxanthin may act as antioxidants in the macular region. (Khachik et al., Invest. Opthalmol. and Vis. Sci., 38, 1802-1811, 1997)

Of the 40 to 50 carotenoids typically consumed in the human diet, lutein and zeaxanthin, are deposited at an up to 5 fold higher content in the macular region of the retina as compared to the peripheral retina. Zeaxanthin is preferentially accumulated in the foveal region, whereas lutein is abundant in the perifoveal region.

Regarding the location of xanthophylls at a cellular level, they are reported to be bound to specific proteins, xanthophylls binding protein (XBP). The XBP is suggested to be involved in the uptake of lutein and zeaxanthin from the blood stream and stabilization of the same in the retina. The study of xanthophylls and XBP by femto-second transient absorption spectroscopy showed better stability for (3R,3'S)-zeaxanthin enriched XBP compared to (3R,3'R)-zeaxanthin while the photophysical properties of the xanthophylls(3R,3'R)-zeaxanthin and (3R, 3'S,meso)-zeaxanthin are generally identical. It is likely that the meso-zeaxanthin is better accommodated with XBP wherein the protein protects the xanthophylls from degradation by free radicals. Thus, the complex may be a better antioxidant than the free xanthophylls, facilitating improved protection of ocular tissue from oxidative damages. (Billsten et al. Photochemistry and Photobiology, 78, 138-145, 2003)

Several functions have been attributed to macular pigments including the reduction of the damaging effects of photo-oxidation from blue light absorbed by the eye, reduction of the effects of light scatter and chromatic aberration on visual performance, and protection against the adverse effects of photochemical reactions because of the antioxidant properties of the carotenoids.

The ability to increase the amount of maculir pigment by dietary supplementation with lutein has been demonstrated (Landrum et al., Dietary Lutein supplementation increases macular pigment, FASEB. J, 10, A242, 1996). The reduced vision function due to cataract and the adult blindness due to AMD can be substantially controlled by consuming fruits and vegetables and dietary supplements containing lutein and zeaxanthin and meso-zeaxanthin available from sea foods denying the vegetarian population. Although meso-zeaxanthin present in eye is considered a metabolic product originating from lutein, the need for dietary supplementation of meso-zeaxanthin is now recognized to improve the macular pigment density.

(Landrum and Bone, Functional Foods and Nutraceuticals, 10 Sep. 2001). Similarly, the study has shown that R,R-zeaxanthin gains entry to blood and finally to macula.

(Breithaupt et al., Brit. J. Nutr. 91, 707-713, 2004). Lutein and zeaxanthin dietary supplements in human trials have been shown to raise the macular pigment density and serum concentrations of these carotenoids (Bone et al., J. Nutr., 133, 992-998, 2003).

Dietary Sources of Lutein and Zeaxanthin

Lutein is a common carotenoid found in most fruits and vegetables, while zeaxanthin in the (R,R)-isomer form is present only in minute quantities in most fruits and vegetables. Dietary sources of zeaxanthin are limited to greens, certain yellow/orange fruits and vegetables such as corn, nectarines, oranges, papaya, persimmons and squash. Capsicum annum is another most common spice widely used which is a good source of zeaxanthin. Wolfberry (*Lycium barbarum, fructus lycii* or Gou Qi Zi) plant has small red berries which are commonly used in Chinese home cooking and has been shown to have a high content of zeaxanthin (mainly as zeaxanthin dipalmitate) but negligible amounts of lutein. The dried fruit of wolfberry is prescribed by Chinese herbalists as a therapeutic agent for a number of eye diseases. In France, lutein dipalmitate (Helenien) isolated from the blossom leafs of Helenium autumnale is reported to be used for the treatment of the visual disorders.

As already mentioned earlier, the dietary source of meso-zeaxanthin is mainly from seafoods like shrimps, fish, turtle, etc, thereby the vegetarian population is deprived of meso-zeaxanthin. However, there are patents available for pharmaceutical compositions containing meso-zeaxanthin for treatment of retinal disorders like increasing the deposition of macular pigments in the human eye and therapeutic treatment or prophylaxis of AMD (Howard et al., U.S. Pat. No. 6,329, 432, 2001).

Lutein and zeaxanthin occur naturally in trans-isomeric form in fruits, vegetables and flowers (marigold). Because of processing conditions due to heat and light, a small percentage of trans- is converted into cis-isomeric form. Therefore, the preferred bio-available form is trans-isomeric as evidenced from the data of geometric isomers compositional analysis of human plasma. (Khachik et al., Isolation and structure elucidation of geometric isomers of lutein, zeaxanthin in extracts of human plasma, J. Chrom. 582, 153-156, 1992). In view of this, it is desirable to use the trans-isomeric form of meso-zeaxanthin in dietary supplements.

To date little is known about the mechanism of formation, uptake and deposition of meso-zeaxanthin in the retina of the eye. Khachik et al. have reported the presence of 2-3% of (3R,3'S, meso)-zeaxanthin in twenty normal human plasma samples and proposed the metabolic pathways of its formation from dietary lutein and zeaxanthin. It is not clear whether the deposition of meso-zeaxanthin in the retina routes through serum or are produced from lutein/zeaxanthin within the retina. (Khachik. et al., in a chapter on Dietary carotenoids and their metabolites as potentially useful chemoprotective agents against cancer, in "Antioxidant food supplement in human health, Eds. Packer et al., Academic Press London, page pp 203-29, 1999). However, Breithaupt et al. did not find the presence of meso-zeaxanthin in human plasma obtained 24 hrs after ingestion of (3R,3'R)-zeaxanthin (ester or free form) in a single blind cross over study using two groups each consisting of six volunteers. The chiral LC-ApcI-MS was used for detection in the pooled plasma sample. (Brit. J. Nutri. 91, 707, 2004)

There is evidence and reasons supporting the hypothesis that the carotenoids lutein, zeaxanthin and meso-zeaxanthin are readily bio-available and consequently increase macular pigment levels (Landrum and Bone, Meso-zeaxanthin-A cutting edge carotenoid, Functional Foods and Nutraceuticals, 10 Sep. 2001).

In present days, there is high demand for xanthophyll crystals containing high amounts of trans-lutein and/or zeaxanthin for its use as antioxidants, prevention of cataract and macular degeneration, as lung cancer-preventive agent, as agents for the absorption of harmful ultra-violet light from sun rays and quencher of photo-induced free radical and reactive oxygen species, etc. A number of commercial products from natural source are now available to facilitate the formulation of industrial and commercial products with lutein or (R,R)-zeaxanthin. However, high concentration (trans, 3R,3'S,meso)-zeaxanthin concentrates, or standardized products for industrial application derived from the same natural source as commercial lutein or zeaxanthin are still not widely available.

As trans-xanthophylls occur naturally in foods with good stability and in greater bio-vailability compared to corresponding cis-isomers, it would be useful for industry and nutritional product formulators to have (trans,3R,3'S,meso)-zeaxanthin from a commercial scale process, made from natural source material same as that which is already accepted by the market for lutein and zeaxanthin products, namely marigold. Unlike products made from synthesis routes, such a trans, meso-zeaxanthin product should be made from safe solvents (GRAS solvents) for producing dietary supplements suitable for human consumption, with minimal solvent residues and specific ratios of lutein and zeaxanthin isomers keeping in mind market requirements.

PRIOR ART

Breithaupt et al. made a comparative study of plasma responses in human subjects after ingestion of (3R,3'R)-zeaxanthin dipalmitate from Wolfberry fruits and non-esterfied (3R,3'R)-zeaxanthin using chiral column HPLC. The study showed an enhanced bio-availability of the ester compared with the non-esterified form. This finding is similar to the earlier observation of β-cryptoxanthin ester absorption. The results also support the existence of an effective enzyme cleaving system for releasing the free xanthophylls from the ester. (Breithaupt et al. J. Nutri. 91, 707-713, 2004).

Khachik et al. have converted lutein into 3'-epilutein and then to (3R,3'R)-zeaxanthin by acid and alkali reaction. The final crystalline material has been shown to consist of 95% (3R,3'R)-zeaxanthin and 5% (3R,3'S)-meso-zeaxanthin, analysed by chiral column HPLC. (J. Nat. Products. 66, 67-72, 2003) The product contains only minor amounts of meso-zeaxanthin This method is also not useful for commercial exploitation for preparing meso-zeaxanthin because the quantity of meso-zeaxanthin produced is very low. In addition the nature of geometrical isomerism of the meso-zeaxanthin produced has not been given.

The functional benefits of zeaxanthin and meso-zeaxanthin as an antioxidant and also their role in the prevention of eye diseases have stimulated the R&D efforts for finding a commercially viable process for production of zeaxanthin and meso-zeaxanthin-rich products which can be used as safe sources of nutritional supplements for human consumption.

While so far meso-zeaxanthin has not been as well recognized as a dietary supplementation ingredient compared to (3R,3'R)-zeaxanthin, it has attracted the attention of health practitioners and pharmacologists who have evinced interest for use of meso-zeaxanthin in formulations for increasing macular pigment density in the human eye and for therapeutic treatment or prophylaxis of diseases and disorders of macula in particular AMD (Howard et al., U.S. Pat. Nos. 6,218,436, 2001; 6,329,432, 2001).

In the U.S. Pat. No. 6,218,436 (2001) a method of prevention of age related macular degeneration in a human subject has been disclosed which comprises orally administering to the subject a sufficient amount of meso-zeaxanthin to increase serum concentration of carotenoids in the subject to at least 0.5 mg/day and maintaining the concentration at that level. This patent does not disclose a composition containing trans, meso-zeaxanthin, (trans, R,R)-zeaxanthin and (trans, R,R)-lutein.

In the U.S. Pat. No. 6,329,432 (2001) a pharmaceutical composition containing an effective dose of meso-zeaxanthin and a carrier or diluent is disclosed. The carrier or diluent may be selected from a carotenoid such as lutein, an isomer of zeaxanthin. The composition may contain at least one compound selected from the group consisting of lutein, (3R,3'R)-zeaxanthin and (3S,3'S)-zeaxanthin In the composition defined in this patent the use of trans, meso-zeaxanthin has not been disclosed Though this patent discloses a composition containing meso-zeaxanthin, lutein and an isomer of zeaxanthin nowhere does it disclose a composition containing trans, meso-zeaxanthin, trans, R,R zeaxanthin & trans, R,R lutein Maoka et al. reported that (3R,3'S)-meso-zeaxanthin occurs naturally in various food sources like fish, shrimps and turtles in addition to (3R,3'R)-zeaxanthin and (3S,3'S)-zeaxanthin isomers. The report includes the occurrence and percentage composition of enantiomeric and (3R,3'S)-meso-zeaxanthin in twenty species of animals. They reported the first isolation of (3R,3'S)-meso-zeaxanthin from fresh samples of biological materials (shrimp, fish and turtle) employing acetone to extract the zeaxanthin fraction followed by transferring to ether-n-hexane mixture and the unsaponifiable matters consisting of carotenoids extracted into ether-n-hexane and chromatographed on MgO-celite to obtain zeaxanthin fraction. The zeaxanthin fraction was converted into benzoate derivatives and separated into pure fractions of (3R,3'R)-Zeaxanthin, (3R,3'S)-meso-zeaxanthin and (3S,3'S)-zeaxanthin by HPLC. The benzoates on saponification gave optically pure zeaxanthins and the identification of each stereoisomer confirmed by UV-Vis. and circular dichroism spectral analysis. (T. Maoka, A. Arai, M. Shimizu and T. Matsuno, Comp. Biochem. Physiol., 83B, 121-124, 1986).

The method of isolation carried out by Maoka et al. from natural source is not commercially feasible for the preparation of (3R,3'S, meso)-zeaxanthin because of the lengthy laborious procedures in isolation and purification of meso-zeaxanthin by chromatographic methods and the associated high costs and low yields Ernst et al. have described the synthesis of (3R,3'S, meso)-zeaxanthin by heating a mixture consisting of (R)-configured phosphonium salt (in slight excess) with C10-dialdehyde monoacetal in butyleneoxide/ethanol, acid catalysed cleavage of acetal and heating of the resultant crude C25-aldehyde with (S)-configured phosphonium salt. The overall yield of (3R,3'S,meso)-zeaxanthin was 79% by crystallization from ethanol with the chemical purity 98% by HPLC and stereochemical purity showing 99% for (3R,3'S, meso)-zeaxanthin with less than 0.3% in each case for (R,R)- and (S,S)-enantiomers. (U.S. Pat. No. 6,743,954, 2004; Pure and Applied Chem. 74, 1369-1382, 2002)

As early as in 1946, Karrer and Jucker reported the sodium ethoxide catalyzed isomerisation reaction of lutein to zeaxanthin (P. Karrer and E. Jucker, Helv. Chim. Acta, 30, 266, 1947). Later in 1971-72 Buchecker et al. assigned R-chirality to lutein based on PMR analysis and attempts to isomerise lutein to R,R-zeaxanthin failed (Chimia, 25, 192, 1971; ibid, 26, 134, 1972).

Andrewes et al. (1974) in the Journal Acta Chem. Scand., B28, 139 (1974) reported the stereo chemical aspects of isomerisation reaction of (3R,3'R, 6R)-lutein (optically active) which resulted in (3R,3'S)-zeaxanthin which was trans-isomeric and optically inactive based on CD spectral studies. The above process results in low yield of 10 to 15% optically inactive (3R,3'S, meso)-zeaxanthin and uses benzene and DMSO which are objectionable for use in food and health supplements.

Rodriguez has described a method of isomerising lutein to yield a mixture of zeaxanthin epimers by employing non aqueous media and heating a mixture of alkali and propylene glycol. Though the circular dichroism spectrum indicated the formation of meso-isomer of zeaxanthin, no attempts were made to quantify the meso-zeaxanthin content and also provide the composition of the isomerised products. (U.S. Pat. No. 5,973,211, 1999).

According to our knowledge, hitherto, xanthophyll composition containing (trans, 3R,3'S,meso)-zeaxanthin, (trans, R,R)-zeaxanthin and (trans, R,R)-lutein is not hitherto reported. Such a composition will be useful for nutrition and health care and as colorants for foods and feeds. Further, there are no available sources of concentrated or purified meso-zeaxanthin for the public other than milligrams available from specialized chemical suppliers for research work.

OBJECTIVES OF THE PRESENT INVENTION

Therefore, the main objective of the present invention is to provide a xanthophyll composition containing (trans,3R,3'S, meso)-zeaxanthin, (trans, R,R)-zeaxanthin and (trans, R,R)-lutein and trace amounts of other carotenoids which is safe for human consumption and useful for nutrition and health care.

Another objective of the present invention is to provide a xanthophyll composition containing at least 50% by weight of total xanthophylls out of which at least 80% is (trans,3R, 3'S,meso)-zeaxanthin, the remaining being (trans, R,R)-zeaxanthin and (trans, R,R)-lutein and trace amounts of other carotenoids.

According to another feature of the present invention there is provided a xanthophyll composition containing at least 80% by weight of total xanthophylls, out of which at least 80% is (trans,3R,3'S, meso)-zeaxanthin, the remaining being (trans, R,R)-lutein, (trans, R, R)-zeaxanthin and trace amounts of other carotenoids.

According to a feature of the present invention, there is provided a xanthophyll composition wherein the composition contains at least 80% by weight of total xanthophylls, out of which at least 50% being (trans, R,R)-zeaxanthin, the remaining being (trans, 3R,3'S, meso)-zeaxanthin, (trans, R,R)-lutein and trace amounts of other carotenoids.

According to a feature of the present invention there is provided a xanthophyll composition wherein the composition contains at least 80% by weight of total xanthophylls, out of which at least 50% being (trans, R,R)-lutein, the remaining being (trans,3R,3'S, meso)-zeaxanthin, (trans, R,R)-zeaxanthin and trace amounts of other carotenoids.

Still another objective of the present invention is to provide a process for the preparation of xanthophyll composition containing (trans,3R,3'S,meso)-zeaxanthin (trans, R,R)-zeaxanthin and (trans, R,R)-lutein and trace amounts of other carotenoids which is safe for human consumption and useful for nutrition and health care.

The above objectives have been achieved by the present invention based on our following findings:
  that the saponification process to convert xanthophyll esters into non-esterified form can be combined with isomerisation of lutein to produce xanthophyll composition containing (trans,3R,3'S,meso)-zeaxanthin, (trans, R,R)-zeaxanthin and (trans, R,R)-lutein and trace amounts of other carotenoids which is safe for human consumption and useful for nutrition and health care;
  that by carrying out the entire process at temperatures in the range of 80-200 degree C. and in the presence of GRAS (Generally Recognized As Safe) reagents and those which can withstand the high temperature, a xanthophyll composition predominantly containing (trans,3R, 3'S,meso)-zeaxanthin can be produced;
  that GRAS reagents employed in the process can be recovered and reused, if required, thereby making the process economical.

SUMMARY OF THE INVENTION

Accordingly, the present invention provides a xanthophyll composition containing (trans,3R,3'S, meso)-zeaxanthin, (trans, R,R)-lutein and (trans, R,R)-zeaxanthin and trace amounts of other carotenoids which is useful for nutrition and health care.

According to another embodiment of the invention there is provided a xanthophyll composition wherein the composition contains at least 50% by weight of total xanthophylls, out of which 80% being (trans,3R,3'S, meso)-zeaxanthin, the remaining being (trans, R,R)-lutein, (trans, R,R,)-zeaxanthin and trace amounts of other carotenoids which is useful for nutrition and health care.

According to another embodiment of the invention there is provided a xanthophyll composition wherein the composition contains at least 80% by weight of total xanthophylls, out of which 80% being (trans,3R,3'S, meso)-zeaxanthin, the remaining being (trans, R,R)-lutein, (trans, R,R,)-zeaxanthin and trace amounts of other carotenoids which is useful for nutrition and health care.

According to yet another embodiment of the present invention there is provided a xanthophyll composition wherein the composition contains at least 80% by weight of total xanthophylls, out of which 45% being (trans,3R,3'S, meso)-zeaxanthin, 50% by weight being (trans, R,R)-zeaxanthin, 5 to 7% being (trans, R,R)-lutein and trace amounts of other carotenoids which is useful for nutrition and health care.

According to still another embodiment there is provided a xanthophyll composition wherein the composition contains at least 80% by weight of total xanthophylls, out of which the (trans,3R,3'S, meso)-zeaxanthin being at least 80%, the amount of (trans, R,R)-lutein being in the range of 5 to 15% and the amount of (trans, R,R)-zeaxanthin being in the range of 5 to 7% and trace amounts of other carotenoids which is useful for nutrition and health care.

According to yet another embodiment of the invention there is provided a xanthophyll composition containing at least 80% by weight of total xanthophylls, out of which at least 50% being (trans, R,R)-zeaxanthin, the remaining being (trans, 3R,3'S,meso)-zeaxanthin, (trans, R,R)-lutein and trace amounts of other carotenoids which is useful for nutrition and health care.

The other carotenoids present in the composition may be those selected from beta-carotene, lycopene, beta-cryptoxanthin, astaxanthin or their mixtures.

The composition of the present invention may be in the form selected from the group of beadlets, micro-encapsulated powders, oil suspensions, liquid dispersions, capsules, pellets, ointments, soft gel capsules, tablets, chewable tablets or lotions/liquid preparations. The composition of the present invention may be provided with a coating which helps preserve the original quality characteristics.

According to another embodiment of the present invention there is provided a process for the preparation of a xanthophyll composition containing (trans,3R,3'S,meso)-zeaxanthin, (trans, R,R)-lutein & (trans, R,R)-zeaxanthin which is useful for nutrition and health care as dietary supplements which comprises:
  (i) mixing lutein or an extract containing lutein ester with GRAS reagent and those which can withstand the temperature of 80 to 200 degree C. and an alkali;
  (ii) heating the resulting mixture under stirring at a temperature in the range of 80-200 degree C. and maintaining the mixture at this temperature for a period in the range of 3 to 36 hrs;
  (iii) if required, adding excess alkali for accelerating the isomerisation reaction;
  (iv) washing with aqueous alcohol and filtering to recover the crude xanthophylls composition containing (trans, 3R,3'S, meso)-zeaxanthin, (trans, R,R)-lutein and (trans, R,R)-zeaxanthin and trace amounts of other carotenoids;

(v) purifying the resulting product by washing with polar and non polar solvents; and (vi) filtering and drying the residue under vacuum.

By varying the reaction temperature, period and the amount of alkali, the composition containing the desired amount of (trans,R,S, meso)-zeaxanthin and trans-lutein can be obtained. However, for preparing the xanthophylls composition containing at least 80% by weight of total xanthophylls, out of which at least 50% by weight being (trans, R,R)-zeaxanthin, the remaining being (trans,3R,3'S, meso)-zeaxanthin, (trans, R,R)-lutein and trace amounts of other carotenoids, the composition prepared as described above has to be mixed with an appropriate amount of (trans, R R)-zeaxanthin.

While selecting the suitable solvent medium in step (i) a variety of criteria are to be taken into consideration. Accordingly, the major criteria to be considered in solvent selection are (i) it should be water immiscible (ii) the solvent should be non-halogenated (iii) the solvent should have GRAS status (iv) the solubility of zeaxanthin in the solvent should be high (v) boiling point of the solvent should be in the range of 80 to 200 degree C. and (vi) stability of zeaxanthin isomers in the solvent used should be high. The solvent which can be employed may be selected from aromatic primary alcohols, especially phenyl carbinol and also p-isobenzyl alcohol.

It should be noted that the solvents in which zeaxanthin is highly soluble such as—chloroform, benzene, DMSO, etc. cannot be used in the process of the present invention because such solvents even in trace amounts are prohibited for human consumption. Hence, the solvent used should fall under GRAS status. It is also to be noted that the stage where the solvent is to be used contains large amounts of water. Therefore, the solvent to be used in the process of invention should be water immiscible so as to facilitate phase separation. Accordingly, many of the solvents which fall under GRAS status and in which lutein-containing material or zeaxanthin is highly soluble cannot be used as such.

The amount of alkali which is used in step (i) may be in the range of 0.5 parts to 1 part of lutein containing material. The alkali used may be selected from sodium/potassium hydroxide and preferably potassium hydroxide.

In a preferred embodiment the step (i) may be carried out under an inert atmosphere, using inert gases such as nitrogen, helium, preferably nitrogen under reduced pressure.

The polar solvent used in step (iv) may be selected from methanol, ethanol. The ratio of alcohol and water used is 0.7:0.3 to 0.8:0.2. The ratio of non-polar solvent and aliphatic alcohol used may be about 0.5:0.5 to 0.8:0.2. The non-polar solvent used may be selected from hexane, heptane, preferably hexane. The alcohol used may be selected from aliphatic alcohols like ethanol, methanol, isopropyl alcohol and mixtures thereof.

BRIEF DESCRIPTION OF DRAWINGS

FIG. 1 is a Chiral HPLC chromatogram of xanthophylls composition containing (trans,R,S)-meso-zeaxanthin sample as described in Example 1.

FIG. 2 is a Chiral HPLC chromatogram of xanthophylls composition containing (trans,R,S)-meso-zeaxanthin sample along with added (trans-3R,3'R,6'R) lutein as described in Example 1.

FIG. 3 is a Chiral HPLC chromatogram of xanthophylls composition containing (trans,R,S)-meso-zeaxanthin sample+(trans-3R,3'R)-zeaxanthin as described in Example 1.

DETAILED DESCRIPTION OF THE INVENTION

The process consists of mixing lutein or an extract containing lutein ester with the solvent such as phenyl carbinol and an alkali such as potassium hydroxide in a three necked vessel fitted with a water condenser and heating the mixture under stirring for a period of 3 to 36 hrs and maintaining the temperature at around 80-200 degree C. It is necessary that sufficient excess alkali is to be used for accelerating the isomerisation reaction. The amount of alkali can be in the range of 0.5 parts to 1 part of the plant extract (oleoresin) or more preferably from 0.5 to 1 part of alkali to one part of saponified oleoresin containing lutein. The reaction time may be 3 to 36 hrs and depends on the temperature used, which may be in the range of 80-200 degree C. and with continuous stirring of the reaction mixture.

At the end of the reaction, the material is taken out and washed with a mixture of alcohol-water preferably 70:30 to remove the excess alkali and other impurities. The crude xanthophyll composition is further washed with non polar hydrocarbon solvent-alcohol mixture, preferably 80:20 filtered and vacuum dried to obtain orange red composition containing (trans,3R,3'S, meso)-zeaxanthin, (trans, R,R)-lutein, (trans, R,R)-zeaxanthin and trace amounts of other carotenoids.

For the identification of (trans,3R,3'S, meso)-zeaxanthin, (trans, R,R)-zeaxanthin & (trans, R,R)-lutein in the composition of the present invention, a chiral HPLC column was used and employing chiral liquid chromatography (LC)-atmospheric pressure chemical ionization ApcI-MS. The xanthophylls present in the composition were quantified by HPLC Model 1100, using a Photo diode array detector (450 nm) and solvent gradient consisting of n-hexane (A) and iso-propanol (B). The column used was a ChiralPak AD, packed with silicagel (10 um), coated with amylose tris-(3,5-dimethylphenylcarbamate) as a selector. The reference standards like (trans,3R, 3'S,meso)-zeaxnthin, (trans,3R,3'R, 6'R)-lutein and (trans,3R,3'R)-zeaxanthin were sourced form Carotenature (Lupsingen, Switzerland).

The following gradient (flow rate 0.7 ml/min.) was used (min. % A 0/94.5; 40/94.5; 50/85; 55/50; 90/50; 91/94.5; 120/94.5.) LC-ApcI-MS was run on a Micromass VG platform II quadrapole mass spectrometer equipped with an ApcI interface, operating in the positive mode (Breithaupt et al., Brit. J. Nutri, 91, 707-713, 2004)).

The spectrophotometric analysis of the xanthophyll composition prepared by the process of the present invention as explained above showed that the total xanthophyll content in the composition is in the range of 50 to 90% by weight (452 nm E1% 2348). The chiral column HPLC analysis of the composition prepared showed that the composition contains >90% by weight of (trans,3R,3'S,meso)-zeaxanthin and the remaining comprising of (trans,R,R)-zeaxanthin and (trans,R,R)-lutein based on HPLC peak areas. FIGS. 1-3 show the chiral HPLC chromatograms of a xanthophylls composition containing (trans,3R,3'S, meso)-zeaxanthin, (trans,3R,3'R)-zeaxanthin and (trans-3R,3'R,6'R)-lutein and the added reference compounds.

In the isomerisation process of lutein to (trans,3R,3'S, meso)-zeaxanthin there is no change in (trans, R,R)-zeaxanthin. In fact (trans, R,R)-zeaxanthin remains practically unaltered during the saponification-isomerization reaction.

In the present invention the solvent used has reaffirmed GRAS status and evidence of safety established. (The FEMA GRAS assessment studies, Adams et al., Food and Chemical Toxicol. 43, 1207(2005)). The process conditions of the present invention are suitable for industrial production of the (trans,3R,3'S, meso)-zeaxanthin containing composition.

The details of the invention are given in the Examples provided below which are provided to illustrate the invention only and therefore should not be construed to limit the scope of the invention

EXAMPLE-1

The oleoresin (100 g) containing 11.2 g total xanthophylls (measured by spectrophotometric method) and (trans,R,R)-lutein and (trans, R,R)-zeaxanthin 69.5 and 5.34% AUC respectively by HPLC analysis was transferred into a three necked RB flask (500 ml capacity) followed by addition of 50 g phenyl carbinol and 50 g potassium hydroxide. To one neck of a RB flask a water condenser was fixed passing water and through the other neck nitrogen gas was bubbled and through the central neck a stirrer was fixed for uniform mixing. The flask was fixed in an oil bath maintaining the temperature of the oil between 100-110 degree C. The reaction of xanthophylls ester saponification and of lutein isomerisation was allowed for 12 hrs after which the resulting red colored product (200 g) was removed and subjected to two stage purification steps, (i) washing with 2 liters of ethanol and water mixture (70/30) to obtain 15 g crude xanthophyll composition containing trans, meso-zeaxanthin, (trans, R,R)-zeaxanthin, (trans, R,R)-lutein and trace amounts of other carotenoids and then (ii) further washing with 300 ml of hexane and IPA mixture (80/20) and) drying under vacuum (30-40 degree C.) to obtain a final xanthophylls composition (3.20 g) containing (trans,3R,3'S, meso)-zeaxanthin, (trans, R,R)-zeaxanthin, (trans, R,R)-lutein and trace amounts of other carotenoids showing total xanthophylls 81.76% by weight by spectrophotometric analysis.

This composition obtained when analysed by chiral column HPLC and LC-ApcI-MS showed the amount of (trans, 3R,3'S, meso)-zeaxanthin to be 90.77% based on the total xanthophyll content, the amount of (trans,R,R)-zeaxanthin to be 5.77% and the amount of (trans, R,R)-lutein to be 3.53% AUC as can be seen from FIG. 1. FIGS. 2 and 3 further show the results from analyzing the composition by chiral column HPLC and LC-ApcI-MS.

EXAMPLE-2

The oleoresin (100 g) containing 8.5 g total xanthophylls (measured by spectrophotometric method) and trans-lutein and trans, zeaxanthin 67 and 5.80% AUC respectively by HPLC was transferred into a three necked RB flask (500 ml capacity) followed by addition of 50 g phenyl carbinol and 50 g potassium hydroxide. To one neck of the RB flask a water condenser was fixed and through the other neck nitrogen gas was bubbled and through the central neck a stirrer was fixed for uniform mixing. The flask was fixed in an oil bath maintaining the temperature of the oil between 100-110 degree C. The reaction of xanthophyll ester saponification and of lutein isomerization were allowed for 12 hrs after which the resulting red colored product (200 g) was removed and subjected to two stage purification steps, (i) washing with 2 liters of ethanol and water mixture (70/30) to obtain 16 g crude xanthophyll crystals containing meso-zeaxanthin product and then (ii) further washing with 300 ml of hexane and IPA mixture (80/20) and drying under vacuum (30-40 degree C.) to obtain a final xanthophyll composition showing 58.69% by weight total xanthophylls by spectrophotometric analysis. The composition when analysed by chiral column HPLC and LC-ApcI-MS to have (trans,3R,3'S, meso) zeaxanthin in an amount of >90% of the total xanthophyll content and the amount of (trans,R,R)-zeaxanthin to be 5% and the amount of (trans,R,R)-lutein to be 3% AUC.

EXAMPLE-3

Oleoresin (100 g) containing 10.2. g total xanthophylls (measured by spectrophotometric method) and trans-lutein and trans, zeaxanthin 69.52 and 4.80% AUC respectively by HPLC was transferred into a three necked RB flask (500 ml capacity) followed by addition of 50 g phenyl carbinol and 30 g potassium hydroxide. To one neck of the RB flask a water condenser was fixed and through the other neck nitrogen gas was bubbled and through the central neck a stirrer was fixed for uniform mixing. The flask was fixed in an oil bath maintaining the temperature of the oil between 100-110 degree C. The reaction of xanthophyll ester saponification and of lutein isomerization were allowed for 8 hrs after which the resulting red colored product (200 g) was removed and subjected to two stage purification steps, (i) washing with 2 liters of ethanol and water mixture (70/30) to obtain 16 g crude xanthophylls crystals containing meso-zeaxanthin product and then (ii) further washing with 300 ml of hexane and IPA mixture (80/20) and drying under vacuum (30-40 degree C.) to obtain a final xanthophyll composition showing 80.26% by weight of total xanthophylls by spectrophotometric analysis. The composition when analysed by chiral HPLC and LC-ApcI-MS was found to have (trans, R,R)-lutein in an amount of >50% of the total xanthophyll content and the amount of (trans,R,S,meso)-zeaxanthin to be 45% and the amount of (trans,R,R)-zeaxanthin to be 5% AUC.

EXAMPLE-4

50 g of Lutemax-free lutein prepared according to our U.S. Pat. No. 6,743,953 was transferred into a three necked RB flask (500 ml capacity). The sample showed 75% by weight total xanthophylls by spectrophotometer method and trans-lutein and trans, zeaxanthin 91 and 8% AUC respectively by HPLC. To this flask 50 g phenyl carbinol and 50 g potassium hydroxide were added and the one neck fitted with water condenser and through the other neck nitrogen gas was bubbled and through the central neck a stirrer was fixed for uniform stirring. The flask was fixed in an oil bath maintaining the temperature of the oil between 108-110 degree C. The isomeric reaction was continued for 18 hrs after which the resulting red colored product (200 g) was removed and subjected to two stage purification steps, (i) The composition was washed with 2 liters of ethanol/water (70/30) to obtain 30 g of crude xanthophyll composition. The composition was further washed with 620 ml of hexane/IPA mixture of (80/20) and dried under vacuum to yield a final xanthophylls composition showing total xanthophylls content 76.52% by weight. This composition was analysed by chiral column HPLC and LC-ApcI-MS and found that it contained (trans,R,S,meso)-zeaxanthin in amount of >90% based on the total xanthophylls content, the amount of (trans,R,R)-zeaxanthin was found to be >5% and the amount of (trans,-R,R)-lutein >3% AUC.

EXAMPLE-5

The marigold oleoresin (100 g) containing 10.5 g total xanthophylls (measured by spectrophotometric method) and trans-lutein and trans,zeaxanthin 67.34 and 5.14% AUC respectively by HPLC was transferred into a three necked RB flask (500 ml capacity) followed by addition of 50 g phenyl carbinol and 50 g potassium hydroxide. To one neck of RB flask water condenser was fixed passing water and through the other neck nitrogen gas was bubbled and through the central neck a stirrer was fixed for uniform mixing. The flask was fixed in an oil bath maintaining the temperature of the oil between 108-110 degree C. The reaction of xanthophyll ester saponification and of lutein isomerization was allowed for 18 hrs after which the resulting red colored product (200 g) was removed and subjected to two stage purification steps, (i) washing with 2 liters of ethanol and water mixture (70/30) and drying under vacuum to obtain 16.2 g crude xanthophylls composition. The composition was then further washed with 300 ml of hexane/IPA mixture (80/20) to obtain xanthophylls composition which was further purified by column chromatography employing silica gel and solvent system hexane/acetone/methanol. The composition showed total xanthophylls 91.66% by weight, by spectrophotometric analysis.

The composition when analysed by chiral column HPLC and LC-ApcI-MS showed that the composition consisted of 92% (trans,3R,3'S,meso)-zeaxanthin out of the total xanthophyll content. The amount of (trans, R,R)-zeaxanthin was found to be 4% and the amount of (trans, R,R)-lutein was found to be 4% based on peak areas.

Advantages of the Invention

1 A simple and effective process of conversion of lutein into a xanthophylls composition rich in trans,meso-zeaxanthin content.
2 The composition has all the essential macular xanthophylls including (trans,3R,3'S,meso)-zeaxanthin, (trans,R,R)-zeaxanthin and (trans,R,R)-lutein and provision for obtaining varying contents of the individual xanthophylls.
3 The xanthophylls composition meets safety considerations because of the use of GRAS reagents and hence is useful for nutrition and dietary supplements for eye health.
4 Both retinyl lutein and lutein in the present case are derived from plant source and both of them undergo a common allylic isomeric rearrangement to form trans,meso-zeaxanthin, thereby establishing similarity and superiority over the one prepared completely by synthetic route.
5 Naturally occurring lutein can be sourced in plenty from marigold flowers, a widely cultivated commercial crop and also the processed products like oleoresin, free lutein and lutein ester.
6. The composition is useful for nutrition and health care and as colorants for food and feeds and is safe for human consumption
7. The use of GRAS reagents employed in the process can be recovered and reused, if required, thereby making the process economical.

We claim:

1. A xanthophyll composition containing (trans, 3R,3'S, meso)-zeaxanthin, (trans, R,R)-lutein and (trans, R,R)-zeaxanthin, and other carotenoids, which are obtained by thermochemical isomerization from lutein and lutein esters or extracts having lutein and lutein esters, and which are useful as dietary supplements, the composition containing at least 80% by weight of (trans, 3R,3'S,meso)-zeaxanthin based on a total xanthophyll content.

2. A xanthophyll composition as claimed in claim 1 wherein the composition contains at least 80% by weight of total xanthophylls, out of which the (trans,3R,3'S, meso)-zeaxanthin content is at least 80%, the remaining being (trans, R,R)-lutein, (trans, R,R)-zeaxanthin and other carotenoids.

3. A xanthophyll composition as claimed in claim 1 wherein the composition contains at least 80% by weight of total xanthophylls, out of which the (trans,3R,3'S, meso)-zeaxanthin content is at least 90%, the remaining being (trans, R,R)-lutein, (trans, R,R)-zeaxanthin and other carotenoids.

4. A xanthophyll composition as claimed in claim 1 wherein the composition contains at least 80% by weight of total xanthophylls, out of which the (trans,3R,3'S, meso)-zeaxanthin content is at least 80%, the amount of (trans, R,R)-lutein being in the range of 5 to 15% and the amount of (trans, R,R)-zeaxanthin being in the range of 5 to 7% and other carotenoids.

5. A xanthophyll composition as claimed in claim 1 wherein the other carotenoids present in the composition is selected from beta-carotene, lycopene, beta-cryptoxanthin, astaxanthin or their mixtures.

6. A composition as claimed in claim 1 wherein the composition is in the form selected from the group of beadlets, micro-encapsulated powders, oil suspensions, liquid dispersions, capsules, pellets, ointments, soft gel capsules, tablets, chewable tablets or lotions/liquid preparations.

7. A process for the preparation of a xanthophyll composition containing (trans,3R,3'S,meso)-zeaxanthin,(trans, R,R)-lutein & (trans, R,R)-zeaxanthin which is useful as a dietary supplement as claimed in claim 1 which comprises:
(i) mixing lutein or an extract containing lutein ester with GRAS solvent and those which can withstand the temperature of 80 to 200 degree C. and an alkali;
(ii) heating the resulting mixture under stirring at a temperature in the range of 80-200 degree C. and maintaining the mixture at this temperature for a period in the range of 3 to 36 hrs;
(iii) washing with aqueous alcohol and filtering to recover the crude xanthophylls composition containing (trans, 3R,3'S,meso)-zeaxanthin, (trans, R,R)-lutein and (trans, R,R)-zeaxanthin and trace amounts of other carotenoids; and
(iv) purifying the resulting product with polar and non polar solvents.

8. A process as claimed in claim 7 wherein the solvent used in step (i) is selected from aromatic primary alcohols, being phenyl carbinol and p-isobenzyl alcohol.

9. A process as claimed in claim 7 wherein the ratio of the lutein material, solvent and the alkali used in step (i) is in the range of 1 to 0.5:0.5 to 1.0:1.0.

10. A process as claimed in claim 7 wherein the ratio of solvent and alkali used in step (ii) is in the range of 0.5:0.5 to 1:1.

11. A process as claimed in claim 7 wherein the alkali used is selected from sodium hydroxide or potassium hydroxide.

12. A process as claimed in claim 7 wherein the steps (i) and (ii) are carried out under an inert atmosphere, using inert gases including nitrogen and helium and under reduced pressure.

13. A process as claimed in claim 7 wherein in step (iii), the alcohol used is selected from methanol, ethanol and the mixtures there of.

14. A process as claimed in claim 7 wherein in step (iii), the ratio of alcohol and water used is in the ratio of 0.7:0.3 to 0.8:0.2.

15. A process as claimed in claim 7 wherein in step (iv) the ratio of non-polar solvent and aliphatic alcohol used is about 0.5:0.5 to 0.8:0.2.

16. A process as claimed in claim 7 wherein in step (iv), the non-polar solvent used is selected from hexane and heptane.

17. A process as claimed in claim 7 wherein in step (iv), the alcohol used is aliphatic alcohol selected from ethanol, methanol, isopropyl alcohol and mixtures thereof.

18. A process for the preparation of a xanthophyll composition containing at least 80% by weight of total xanthophylls, out of which at least 50% being (trans, R,R)-zeaxanthin, the remaining being (trans,3R,3'S, meso)-zeaxanthin, (trans, R,R)-lutein and other carotenoids which comprises mixing the composition as claimed in claim 2 with appropriate amount of (trans, R,R)-zeaxanthin.

19. A process for the preparation of a xanthophyll composition containing (trans, 3R,3'S, meso)-zeaxanthin, (trans, R,R)-lutein & (trans, R,R)-zeaxanthin which is useful as a dietary supplement as claimed in process claim 11 which comprises: if required, adding excess alkali for accelerating the isomerisation reaction.

20. A process for the preparation of a xanthophyll composition containing (trans,3R,3'S,meso)-zeaxanthin, (trans, R,R)-lutein & (trans, R,R)-zeaxanthin which is useful as a dietary supplement as claimed in process claim 11 which comprises: filtering and drying the resulting product under vacuum and collecting xanthophylls composition containing (trans,3R,3'S,meso)-zeaxanthin.

21. A xanthophyll composition as claimed in claim 1 wherein the composition contains at least 95% by weight of a combination of (trans 2R,3'S,meso)-zeaxanthin and (trans R,R')-zeaxanthin relative to the total xanthophyll content.

22. A process as claimed in claim 20, wherein the drying is effected in vacuum at a temperature in the range of 30 degrees to 40 degrees C. for a period ranging from 48 to 72 hours.

* * * * *